United States Patent

Long et al.

[11] Patent Number: 6,030,403
[45] Date of Patent: Feb. 29, 2000

[54] METHOD AND APPARATUS FOR APPLYING ELECTRICAL ENERGY TO MEDICAL INSTRUMENTS

[75] Inventors: Gary L. Long, Cincinnati; Lynetta J. Freeman, West Chester, both of Ohio; Bryan D. Knodel, Flagstaff, Ariz.

[73] Assignee: Ethicon Endo-Surgery, Inc., Cincinnatti, Ohio

[21] Appl. No.: 09/271,775

[22] Filed: Mar. 18, 1999

Related U.S. Application Data

[62] Division of application No. 08/856,534, May 14, 1997.

[51] Int. Cl.[7] .................................................. A61B 17/34
[52] U.S. Cl. ........................................ 606/185; 604/164
[58] Field of Search .................... 606/185, 170, 606/38, 28, 32; 604/185, 164, 167; 607/122

[56] References Cited

U.S. PATENT DOCUMENTS

| | | | |
|---|---|---|---|
| 1,620,929 | 3/1927 | Wallerich . | |
| 4,535,773 | 8/1985 | Yoon | 604/51 |
| 4,674,010 | 6/1987 | Van den Steen | 361/433 |
| 4,717,438 | 1/1988 | Benge et al. | 156/152 |
| 4,799,480 | 1/1989 | Abraham et al. | 128/303.13 |
| 4,825,217 | 4/1989 | Choi | 343/135 |
| 4,884,982 | 12/1989 | Fleming et al. | 439/620 |
| 4,934,960 | 6/1990 | Capp et al. | 439/620 |
| 4,936,842 | 6/1990 | D'Amelio et al. | 606/42 |
| 5,105,829 | 4/1992 | Fabian et al. | 128/899 |
| 5,124,509 | 6/1992 | Hoendervoogt et al. | 178/19 |
| 5,342,356 | 8/1994 | Ellman et al. | 606/32 |
| 5,344,420 | 9/1994 | Hilal et al. | 606/28 |
| 5,380,321 | 1/1995 | Yoon | 606/41 |
| 5,383,860 | 1/1995 | Lau | 604/167 |
| 5,387,196 | 2/1995 | Smith et al. | 604/164 |
| 5,387,197 | 2/1995 | Smith et al. | 604/164 |
| 5,391,166 | 2/1995 | Eggers | 606/48 |
| 5,403,312 | 4/1995 | Yates et al. | 606/50 |
| 5,417,687 | 5/1995 | Nardella et al. | 606/32 |
| 5,432,486 | 7/1995 | Wong | 333/109 |
| 5,437,277 | 8/1995 | Dumoulin et al. | 128/652.1 |
| 5,437,662 | 8/1995 | Nardella | 606/40 |
| 5,443,462 | 8/1995 | Hannant | 606/34 |
| 5,445,142 | 8/1995 | Hassler, Jr. | 600/105 |
| 5,540,684 | 7/1996 | Hassler, Jr. | 606/40 |
| 5,545,142 | 8/1996 | Stephens et al. | 604/167 |
| 5,562,611 | 10/1996 | Transue | 604/158 |
| 5,591,192 | 1/1997 | Privitera et al. | 606/185 |
| 5,597,107 | 1/1997 | Knodel et al. | 227/175.2 |
| 5,599,348 | 2/1997 | Gentelia et al. | 604/35 |
| 5,605,539 | 2/1997 | Buelna et al. | 604/51 |
| 5,625,537 | 4/1997 | Neuder | 361/775 |
| 5,733,323 | 3/1998 | Buck et al. | 607/122 |

*Primary Examiner*—Michael Buiz
*Assistant Examiner*—Kevin Truong
*Attorney, Agent, or Firm*—Bernard Shay

[57] ABSTRACT

A safety-shielded trocar having an obturator with a linear cutting edge surface defining a base width substantially less than the diameter of the safety shield is disclosed. When the trocar is inserted through tissue, the tissue dilates from the width of the linear incision to accommodate the size of the safety shield of the trocar, thus making it possible to provide an access opening greater than the incisional width made by the linear cutting edge surface of the obturator. In a preferred embodiment, the safety shield has a shield tip region which is asymmetric to facilitate the dilation of the tissue as the trocar is inserted.

2 Claims, 5 Drawing Sheets

METHOD AND APPARATUS FOR APPLYING ELECTRICAL ENERGY TO MEDICAL INSTRUMENTS

This is a divisional of application Ser. No. 08/856,534, filed May 14, 1997 now pending.

FIELD OF THE INVENTION

The present invention relates, in general, to an improved electrosurgical instrument and method of use and, more particularly, to an electrosurgical trocar adapted to provide electrosurgical energy to specially adapted cordless electrosurgical instruments used with the electrosurgical trocar and to a method of using such a trocar and associated instruments.

BACKGROUND OF THE INVENTION

The surgical trocar has become the mainstay in the development and acceptance of endoscopic surgical procedures. Endoscopic surgery involves the performance of surgery through a number of openings having a relatively small diameter. These openings are made with the trocar, which typically includes a trocar obturator and a trocar cannula. The obturator is the piercing implement which punctures the body wall to make the opening. Once the puncture is made, the obturator is withdrawn from the cannula. The cannula then provides a small diameter passageway into and through the body wall to provide access for additional surgical instrumentation to the surgical site. The function, structure and operation of a typical trocar is described in detail in U.S. Pat. No 5,387,197, which is hereby incorporated herein by reference.

Such additional surgical instruments may include, for example, bipolar or monopolar electrosurgical instruments which utilize radio frequency electrosurgical energy. Known electrosurgical instruments include, for example, bipolar forceps, bipolar scissors, monopolar-hook monopolar-scissors and, bipolar endocutters. Each of those instruments has an electrosurgical end effector which is adapted to treat tissue through the application of electrosurgical (e.g. radio frequency or RF) energy to tissue which is brought in contact with the electrosurgical end effector. Most known electrosurgical instruments are connected by electrical cords to electrosurgical generators. The structure and operation of a typical bipolar cutter/stapler ("bipolar endocutter") is described in U.S. Pat. No. 5,403,312 which is hereby incorporated herein by reference.

Electrosurgical generators, such as the Force 11 generator which is available from Valleylab of Bolder Colo., supply electrical energy to the electrosurgical instruments through electrical cords. The electrical cords, being attached directly to the electrosurgical instrument, may make the electrosurgical instrument inconvenient to use. Alternatively, electrical cords may cause undesirable delays as one electrosurgical instrument is unplugged from the generator and another is plugged in. Thus, it would be advantageous to design a cordless electrosurgical instrument. However, such a cordless electrosurgical instrument would have to be connected to the electrosurgical generator through some alternate arrangement. Therefore, it would also be advantageous to design a trocar or a trocar adapter which is adapted to conduct electrosurgical energy to specially designed cordless electrosurgical instruments.

SUMMARY OF THE INVENTION

In the present invention, a surgical trocar is adapted to conduct electrosurgical energy to specially adapted cordless electrosurgical instruments. In one embodiment of the present invention, an electrosurgical trocar includes a cannula, an electrosurgical adapter and a locking connector adapted to connect the cannula to the electrosurgical adapter. The cannula is an elongated tube which may be inserted into a body cavity, duct or vessel. The electrosurgical adapter includes a housing with an elongated central aperture, first and second electrical contacts positioned in and extending axially along the elongated aperture, first and second electrical conductors, first and second external conductors, a compression mechanism, an outer housing and an electrical cord.

In a further embodiment of the present invention, the adapter aperture is formed by an aperture wall positioned in the adapter housing. The first and second electrical contacts are positioned in and extend axially along the aperture, forming at least a portion of the walls of the aperture. The first and second electrical conductors connect the first and second electrical contacts to the first and second external connectors. The compression mechanism biases the first and second electrical contacts toward the center of the adapter aperture. An electrical cord is connected to the first and second external connectors such that the electrical cord may be used to plug the adapter into an electrosurgical generator.

In a further embodiment of the present invention, the first electrical contact is a first stator plate and the second electrical contact is a second stator plate. The second stator plate is positioned opposite the first stator plate. The second stator plate is electrically insulated from the first stator plate. The compression member includes one or more compression rings positioned around the first and second electrical contacts.

In a further embodiment of the present invention, the electrosurgical trocar includes a locking connector which connects the cannula to the adapter. In this embodiment of the invention, the adapter includes first and second locking cleats extending from the distal end of the connector. The cannula includes receptors such as indentations or ribs which hold the distal ends of the locking cleats in place, thus holding the connector in contact with the cannula.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
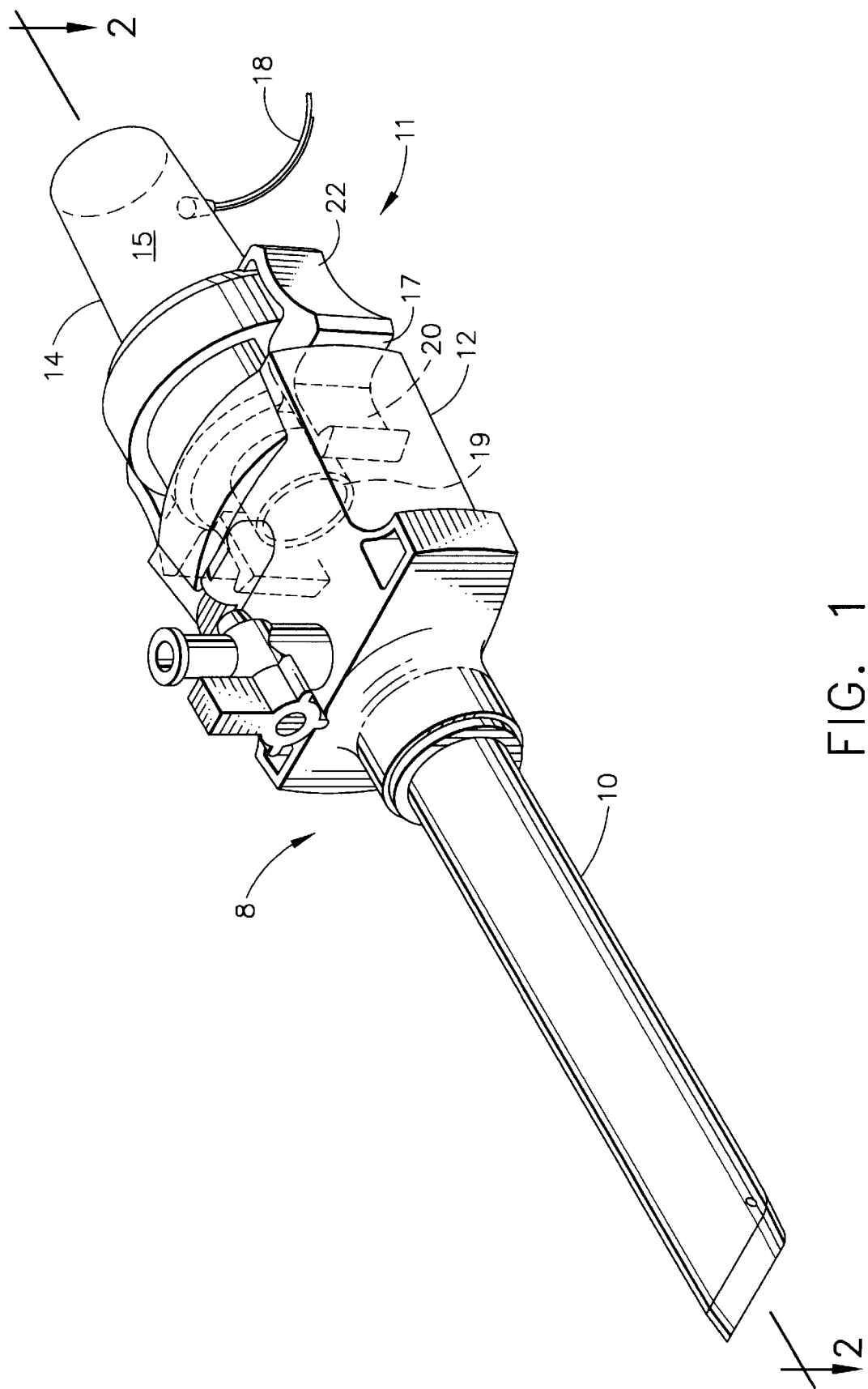
FIG. 1 is a perspective view of an electrosurgical trocar according to the present invention.

FIG. 1 is a perspective view of an electrosurgical trocar according to the present invention. Electrosurgical trocar 11 includes trocar cannula 8 and electrosurgical adapter 14.

Electrosurgical trocar 11 may also include an obturator assembly (not shown) such as the one illustrated in U.S. Pat. No. 5,387,197, which has been previously incorporated herein by reference. Trocar cannula 8 includes cannula housing 12 and cannula tube 10, extending from housing 12. Electrosurgical adapter 14 includes an adapter housing 15, locking connector 17 and an electric cord 18. In the embodiment of the invention illustrated in FIG. 1, electrosurgical adapter 18 is connected to trocar cannula 8 by locking connector 17. Locking connector 17 includes locking cleat 20 and release button 22. It will be apparent that electrosurgical adapter 18 may be integrated directly into trocar cannula 8, thus eliminating the need for locking connector 17.

Figure 2:
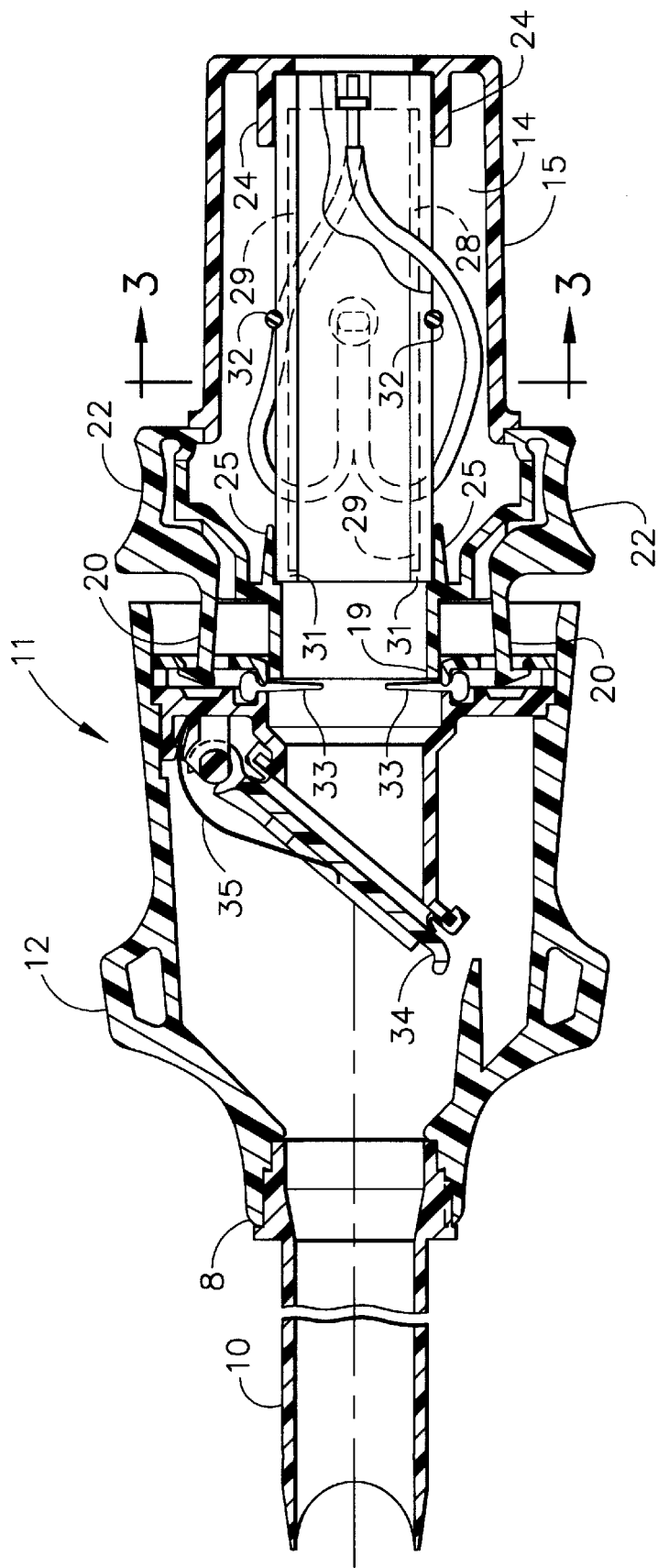
FIG. 2 is a plan view section taken through the electrosurgical trocar illustrated in FIG. 1.

FIG. 2 is a plan view section taken through electrosurgical trocar 11. In FIG. 2, cannula housing 12 includes flapper valve 34 and ring gasket 35. Electrosurgical adapter 14 includes central aperture 19, front flange 25 and base flange 24. Aperture 19 is an elongated aperture for receiving working instruments such as endoscopic electrosurgical instruments. Electrosurgical adapter 14 further includes a plurality of interior electrical contacts which, in the embodiment illustrated in FIGS. 2 and 3, comprise stator plates 28 and 29. At least a portion of the interior wall of central aperture 19 is formed by upper insulator 30 and upper stator plate 28. Upper insulator 30 is positioned against front flange 25 and base flange 24. Compression member 32 is, in the present embodiment, an o-ring which is positioned outside of upper insulator 30 to bias upper insulator 30 and upper stator plate 28 toward the center of central aperture 19. Compression member 32 may also be, for example, a spring, a flexible sleeve, a plurality of o-rings or any other suitable biasing member.

Figure 3:
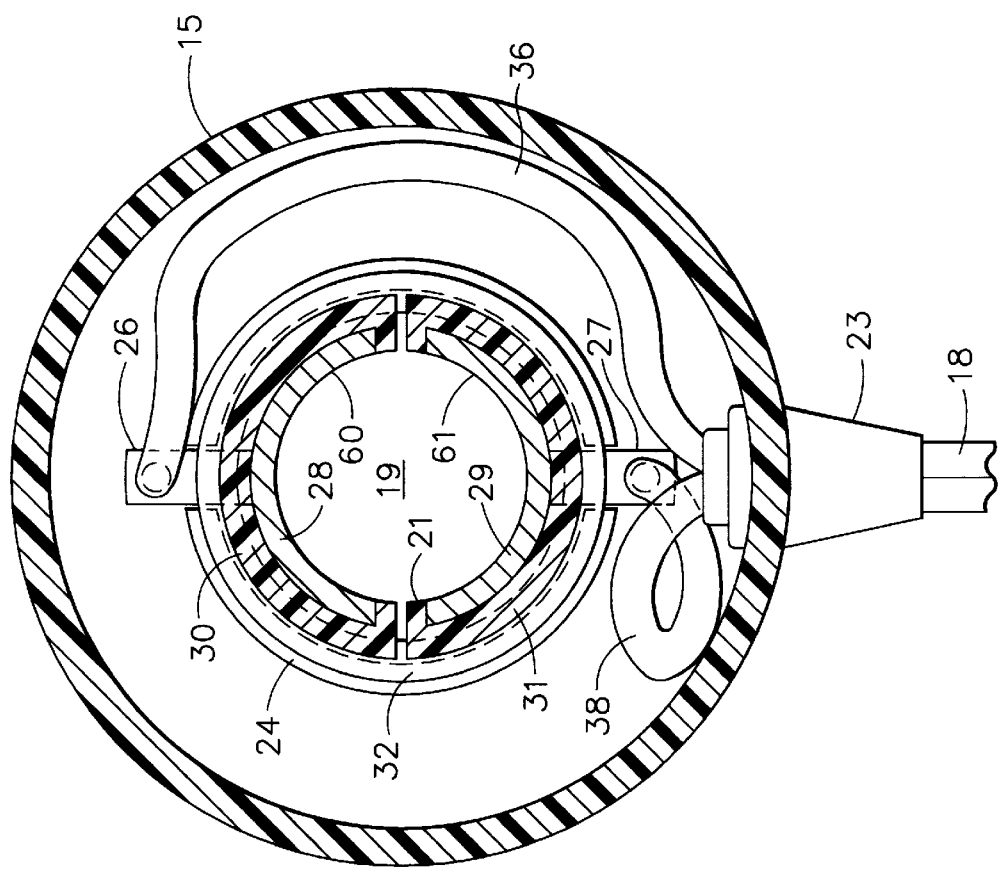
FIG. 3 is a section view taken along line 3—3 of FIG. 2.

FIG. 3 is a sectional view of electrosurgical adapter 14 taken along line 3—3 of FIG. 2. Central aperture 19 is defined by aperture interior wall 21. The portion of interior wall 21 visible in FIG. 3 is formed, at least in part, by upper contact surface 60 of upper stator plate 28 and lower contact surface 61 of lower stator plate 29. Upper stator plate 28 and lower stator plate 29 are positioned on, and electrically insulated from one another by, upper insulator 30 and lower insulator 31, respectively. Compression member 32 surrounds upper insulator 30 and lower insulator 31. Compression member 32, which is an o-ring in the embodiment of FIGS. 2–3, biases upper insulator 30 and lower insulator 31 toward the center of central aperture 19. Electric cord 18 is connected to upper stator plate 28 by upper conductor 36 and upper stator tab 26. Electric cord 18 is connected to lower stator plate 29 by lower conductor 38 and lower stator tab 27. Base flange 24, which is part of adapter housing 15, holds upper insulator 30 and lower insulator 31 in place. Strain relief 23 protects electric cord 18 as it passes through adapter housing 15.

Figure 4:
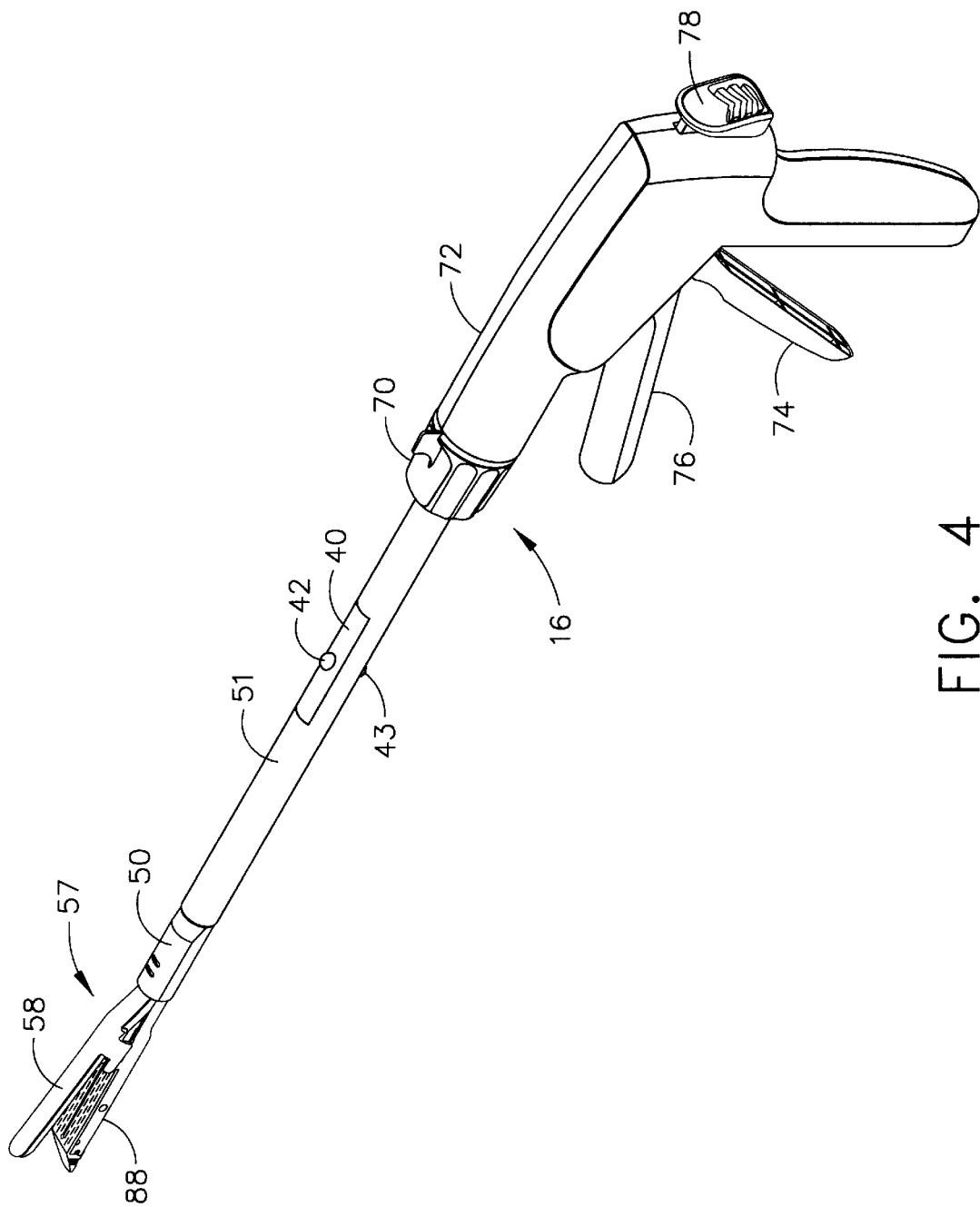
FIG. 4 is a perspective view of a cordless electrosurgical instrument according to the present invention.

FIG. 4 is a perspective view of a cordless electrosurgical instrument which may be, for example, a bipolar cutter/stapler. In FIG. 4, electrosurgical instrument 16 includes handle 72, closure tube 50 and bipolar end effector 57. Closure tube 50 is elongated to facilitate insertion of end effector 57 through a trocar cannula, thus facilitating the use of electrosurgical instrument 16 in endoscopic or laparoscopic surgical procedures. Handle 72, which is located at the proximal end of instrument 16, includes grasping trigger 74, firing trigger 76 and release trigger 78. Closure tube 20, which connects handle 72 to end effector 57, includes rotation knob 70, first contact insulator 40, first instrument electrode contact 42, second instrument electrode contact 43 and outer tube 51. End effector 57, which is located at the distal end of closure tube 50 includes anvil 58 and cartridge channel 88. Electrosurgical instrument 16 is similar in structure and operation to the bipolar endoscopic electrocautery linear cutting and stapling instrument illustrated and described in U.S. Pat. No. 5,403,312, which has been previously incorporated herein by reference. However electrosurgical instrument 16 is cordless. In electrosurgical instrument 16, electrosurgical energy is supplied to the instrument through first instrument electrode contact 42 and second instrument electrode contact 43.

Figure 5:
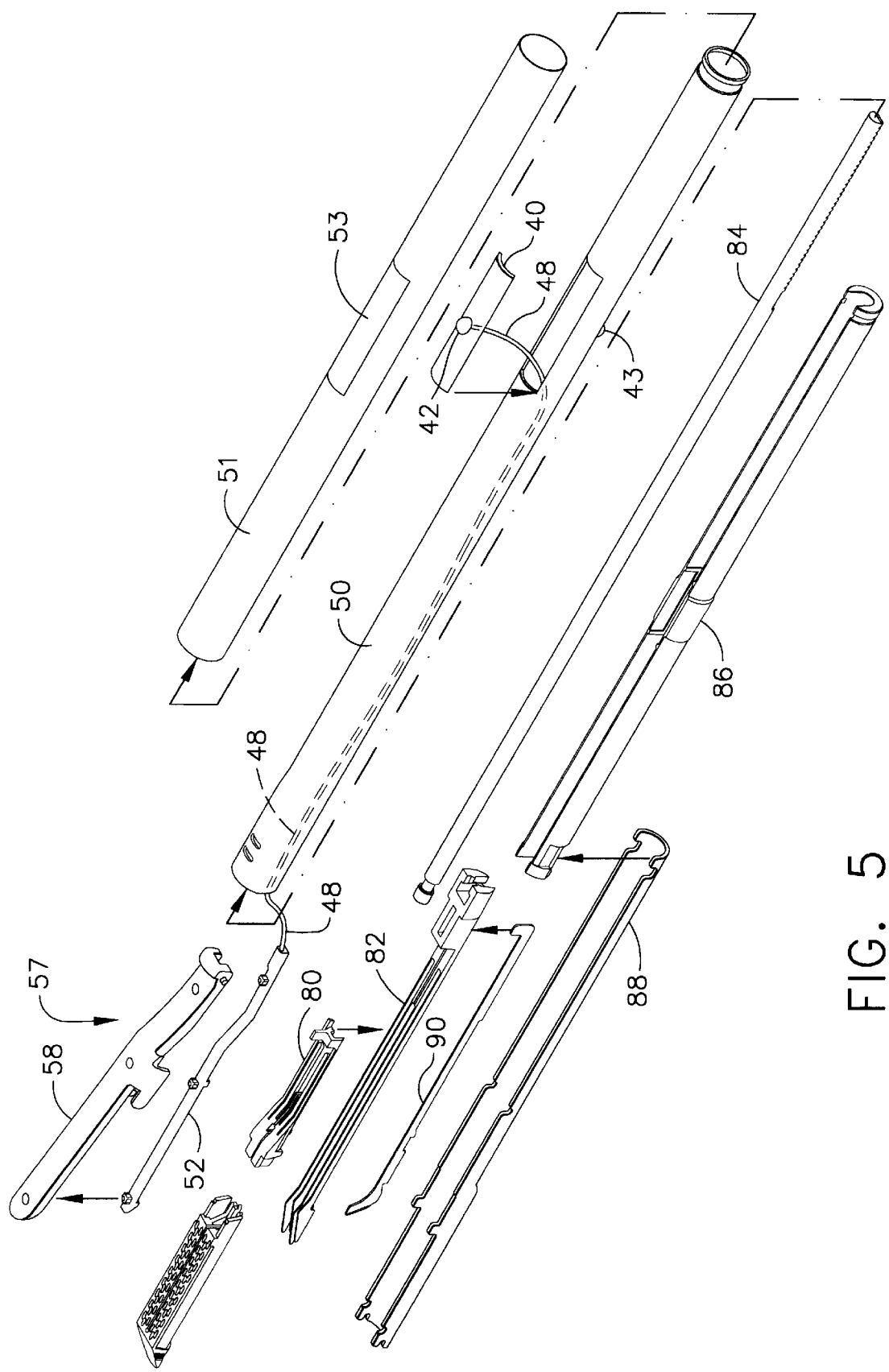
FIG. 5 is an exploded perspective view of the distal end of the cordless electrosurgical instrument illustrated in FIG. 4.

FIG. 5 is an exploded perspective view of the in the distal end of electrosurgical instrument 16. In FIG. 5, outer tube 51 is positioned over closure tube 50. In the instruments illustrated in FIGS. 4 and 5, closure tube 50 is electrically conductive and outer tube 51 is constructed of an electrically insulating material. In the instruments illustrated in FIGS. 4 and 5, closure tube 50 is electrically conductive and outer tube 51 is constructed of an electrically insulating material. First instrument electrode contact 42, which penetrates first contact insulator 40, extends through opening 53 in outer tube 51. First contact insulator 40 electrically isolates contact 42 from closure tube 50. Second instrument electrode contact 43 which is connected to and in electrical contact with closure tube 50, extends through a second opening (not shown) in outer tube 51. In an alternate electrosurgical instrument, contact 43 could be connected to an electrode on end effector 57 by an insulated wire which runs through closure tube 50 and, in such an instrument, closure tube 50 may be constructed of an insulating material. Conductor 48 passes through closure tube 51 from electrode assembly 52 to first instrument electrode contact 40, electrically connecting electrode assembly 52 to contact 40. Electrode assembly 58 is positioned in anvil 58. Electrode assembly 52 may be electrically insulated from anvil 58 and closure tube 50 to prevent electrode assembly 52 from shorting to anvil 58 or closure tube 50. Conductor 48 may be insulated to prevent it from shorting with closure tube 50 or any of the mechanism in closure tube 50.

In the cordless electrosurgical instrument illustrated in FIGS. 4 and 5, knife 90 is connected to wedge assembly 82 and wedge assembly 82 is connected to firing rod 84, which, in turn, is operatively connected to firing trigger 76. Closure tube 50 is operatively connected to rotation knob 70, grasping trigger 74 and release trigger 78. Wedge guide 80 is fitted over wedge block assembly 80 to guide wedge block assembly 80 as firing rod 84 moves wedge block assembly 82. The structure and operation of the mechanical features of the device illustrated in FIGS. 4 and 5 may be better understood with reference to the mechanical cutting and stapling instrument illustrated and described in U.S. Pat. No. 5,597,107 which is hereby incorporated herein by reference.

In the device illustrated in FIGS. 4 and 5, cartridge channel 88 and outer tube 51 are electrically conductive and in electrical contact. Thus, where electrode assembly 52 acts as a primary electrode, cartridge channel 88 acts as a second or return electrode. When electrically conductive tissue is grasped by end effector 57 and an electrosurgical generator is connected to first instrument electrode contact 42 and second instrument electrode contact 43, electrosurgical energy will flow through the grasped tissue, coagulating the grasped tissue.

In operation, trocar cannula 8 is used with a conventional trocar orbitor (not shown) to penetrate the wall of a body cavity such as, for example, the abdominal wall of a human being. After the body wall is penetrated, the obturator assembly is withdrawn from trocar cannula 8, and the cannula is used as an access portal for the passage of various endoscopic instruments to provide access to internal organs. Where the endoscopic instrument to be used is a cordless electrosurgical instrument such as electrosurgical instrument 16, electrosurgical adapter 14 may be attached to trocar cannula 8. Once electrosurgical adapter 14 is attached to trocar cannula 8 and electric cord 18 is attached to a suitable electrosurgical generator (not shown), electrosurgical trocar 11 may be used to provide electrosurgical energy to cordless electrosurgical instruments such as electrosurgical instrument 16.

When a cordless electrosurgical instrument such as electrosurgical instrument 16 is inserted into a body cavity through electrosurgical trocar 11, end effector 57 passes through cannula 8 and into the body cavity while most of closure tube 50 remains in the trocar. Handle 72, which is outside of trocar 11, is manipulated by the surgeon to control the position of end effector 57.

Electrosurgical energy is provided to instrument 16 by the interaction of contact 42 and contact 43 with the stator plates 28 and 29. The diameter of central aperture 19 generally corresponds with the outer diameter of closure tube 50, including outer tube 51, so that closure tube 50 slides through central aperture 19 and the interior of cannula tube 10. Contact 42 and contact 43, being raised above the surface of closure tube 50 and outer tube 51, will scrape against stator plates 28 and 29 as closure tube 50 passes through aperture 19. Compression member 32 will ensure that stator plates 28 and 29 maintain contact with contacts 42 and 43, maintaining a good electrical connection between the stator plates in adapter 14 and the contact points on instrument 16. Electrical contact will be maintained so long as contacts 42 and 43 are positioned in central aperture 19 opposite stator plates 28 and 29.

With contacts 42 and 43 in contact with stator plates 28 and 29, electrosurgical energy may be supplied to electrosurgical trocar 11 through electric cord 18. The electrosurgical energy passes through conductors 36 and 38, stator tabs 26 and 27 and stator plates 28 and 29 into instrument 16 via contacts 42 and 43. Electrosurgical energy supplied to instrument 16 via contacts 42 and 43 may be supplied to end effector 57 via the circuit formed by first instrument electrode contact 42, conductor 48, electrode assembly 52, cartridge channel 88, closure tube 50 and second instrument electrode contact 43. This circuit is completed when tissue or other conductive tissue is grasped by end effector 57, providing a path from electrode assembly 52 to cartridge channel 88.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An electrosurgical trocar, said trocar comprising:
   a) a cannula
   b) an electrosurgical adapter adapted to supply electrosurgical energy to instruments positioned in said cannula; and
   c) a locking connector adapted to connect said cannula to said adapter.

2. An electrosurgical trocar according to claim 1, wherein said locking connector comprises:
   a) first and second locking cleats extending from a first end of said adapter; and
   b) first and second indentations on said cannula.

* * * * *